United States Patent [19]

Blasnik

[11] Patent Number: 5,437,685
[45] Date of Patent: * Aug. 1, 1995

[54] STERNUM BANDING ASSEMBLY

[76] Inventor: William Blasnik, 1512 Palisade Ave., Fort Lee, N.J. 07024

[ * ] Notice: The portion of the term of this patent subsequent to Nov. 22, 2011 has been disclaimed.

[21] Appl. No.: 219,912

[22] Filed: Mar. 30, 1994

Related U.S. Application Data

[62] Division of Ser. No. 8,603, Jan. 25, 1993, Pat. No. 5,366,461.

[51] Int. Cl.⁶ .............................................. A61B 17/82
[52] U.S. Cl. ..................................... 606/151; 606/74; 24/200 W
[58] Field of Search ............... 606/151, 157, 191, 213, 606/215, 216, 218, 74; 24/20 W, 200 W, 23 W

[56] References Cited

U.S. PATENT DOCUMENTS

| | | | |
|---|---|---|---|
| 3,000,433 | 9/1961 | Kemper | 24/23 W |
| 4,015,311 | 4/1977 | Curtis | 24/23 W |
| 4,535,764 | 8/1985 | Ebert | 606/74 |
| 4,730,615 | 3/1988 | Sutherland et al. | |
| 4,813,416 | 3/1989 | Pollak et al. | 606/74 |
| 4,991,266 | 2/1991 | Oetiker | 24/200 W |

Primary Examiner—Tamara L. Graysay
Attorney, Agent, or Firm—James & Franklin; Harold James; Robert L. Epstein

[57] ABSTRACT

A banding assembly has a needle at one end, a long thin band, and a buckle at the other end. The buckle is provided with upstanding elements on either side of a channel which receives the band. The elements have openings adapted to be engaged by a towel clamp to retain the buckle as the band is drawn through the channel and locks into position. The elements are normally spaced apart by a distance slightly less than the width of the band. Once locked into place, the band is trimmed, leaving a tail extending from the buckle. The tail is bent backwards and "snap fits" between the elements. The elements are then crimped over the tail to retain it on the buckle and to cover any sharp edges. A dome-like member is provided to guide the band into the channel. The buckle is attached to the end of the band by spaced tabs which extend through openings in the band and are crimped toward each other.

10 Claims, 4 Drawing Sheets

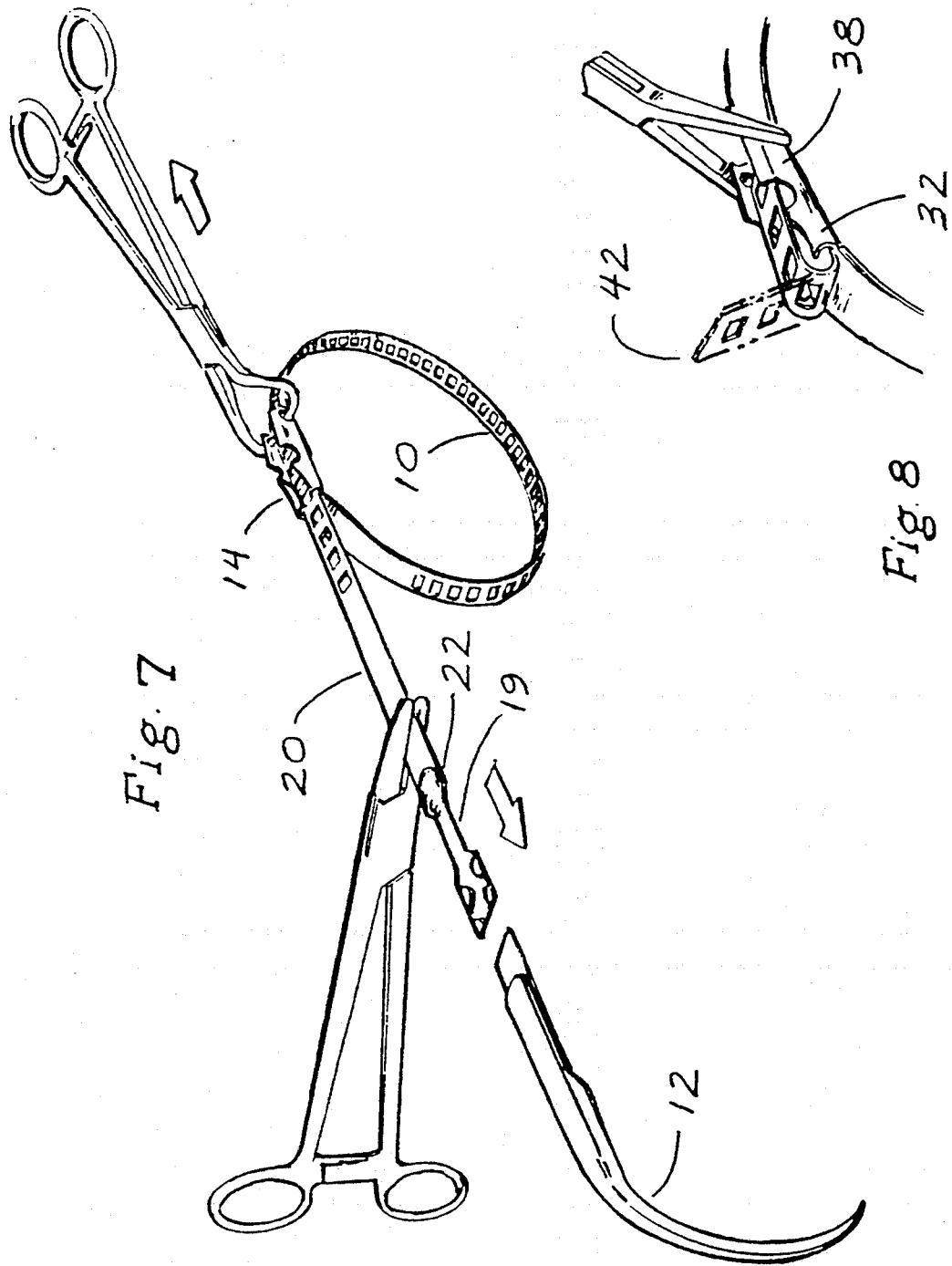

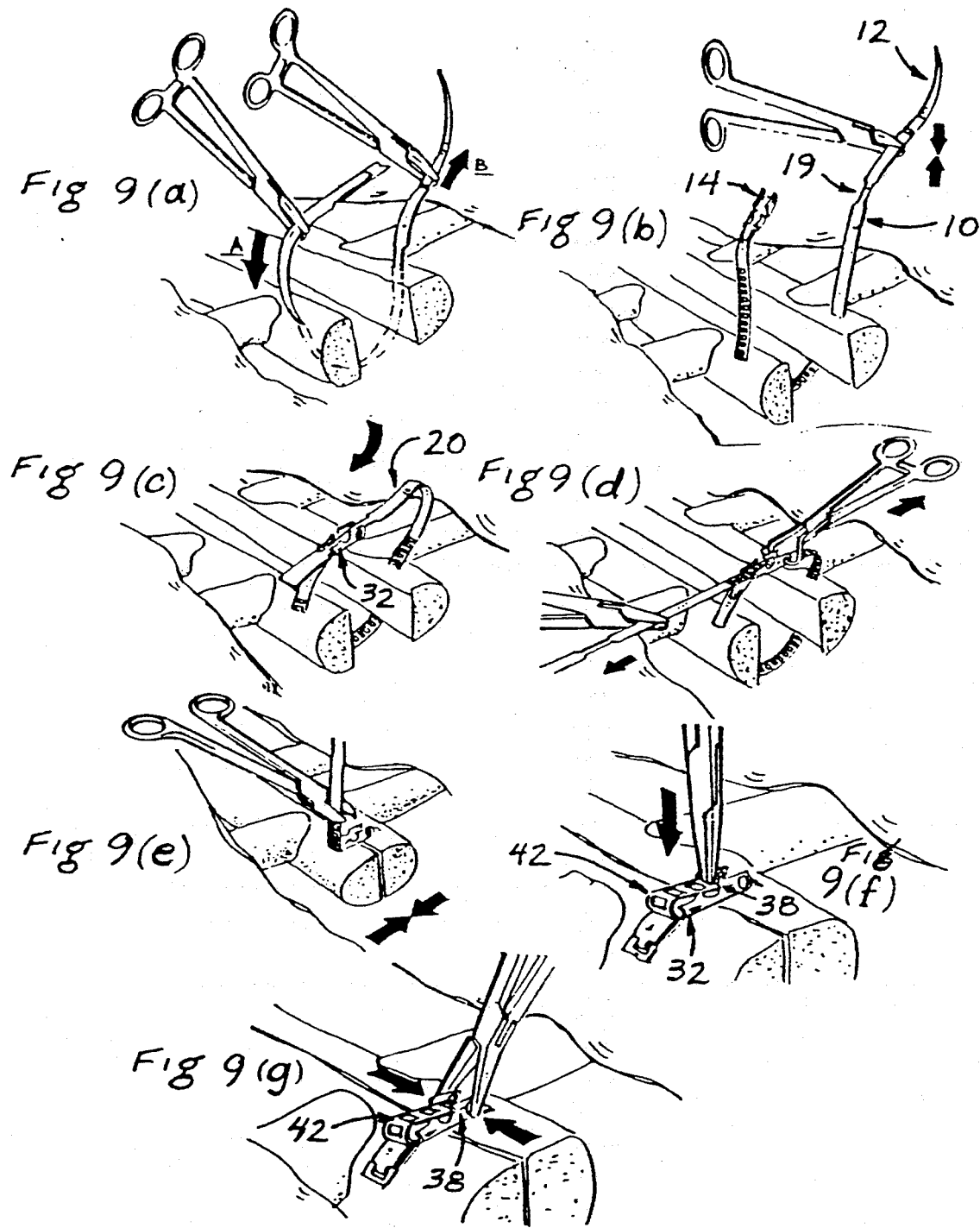

STERNUM BANDING ASSEMBLY

This is a divisional of Ser. No. 08/008,603 filed Jan. 25, 1993, now U.S. Pat. No. 5,366,4.

The present invention relates to surgical devices and more particularly to an improved banding assembly for clamping and closing the split halves of the sternum as part of surgery which involves a median sternotomy, such as open heart surgery.

For proper healing of the split sternum, the surgically opened faces must be approximated, compressed and held together rigidly. This task is complicated by the physiological role of the sternum. The sternum is a functional component of the thoracic cage and, with the costal cartilages, serves as the hinge for the "bucket handle" action of the ribs during respiration. The incessant motion of the rib cage transmits continuous stresses across the sternum. Any method of closing a split sternum must be able to maintain compression and rigidity across the closure in the face of these constant stresses.

One technique used in the past involves closing the sternum with a plurality of spaced stainless steel wires. Five or more 20 gauge stainless steel wires are placed either parasternally (around the sternum) or transternally (through the sternum) using a large, swaged-on cutting needle. The needles are cut off and the sternal halves are approximated by twisting the wires. Finally the wires are cut short and the ends are tucked into the adjacent tissue.

While this is a useful surgical technique for closing the sternum, there are certain problems associated with this procedure. The wires are difficult to place and if to be placed transternally, the needle must be driven through the sternum, a very difficult task. The internal mammary artery is subject to being injured during the procedure. Also, the sharp wires often cause cutting of surgical gloves and may injure the surgeon. Twisting the wires while tightening may produce torsional stresses and may even severely weaken or fracture the wires. The stresses imparted by respiratory motion of the chest cage can further fatigue or break the wires. The wires may also slice through thin or osteoporotic bone. Hence closure of the sternum with wires is a slow and tedious if not dangerous technique.

To overcome the drawbacks of conventional wire banding, it has been proposed to use a board in front of the sternum through which the wires pass. Others have suggested replacing the wires with various types of clamps or closures.

Presently, the best system seems to be to employ flat flexible stainless steel bands instead of wires. Each band may be formed integrally with a surgical needle at one end and a locking member at the other end. One type of such band is disclosed in U.S. Pat. No. 4,535,764 to Ebert. However, Ebert's locking member requires that the band be threaded through an opening in the locking member and bent back over the member and threaded through two other openings, a complicated and time consuming task. Another variation is disclosed in U.S. Pat. No. 4,730,615 to Sutherland. Sutherland uses a polymer coated metal band with an upstanding head. Adjacent the head is a serrated spine portion which is locked by a metal finger on a channel in the head.

A significant improvement over the assemblies taught by Sutherland and Ebert is the bonding or banding assembly disclosed in U.S. Pat. No. 4,813,416, issued to me and to Stanley Pollak. That banding assembly includes a locking member in the form of a buckle. The buckle has a loop segment under the saddle. The segment terminates in a spring tooth adapted to engage an opening in the band when the band is pulled through a channel. The channel is defined by "C" shaped flanges extending upwardly from either side of the saddle.

In spite of the success of the band disclosed in U.S. Pat. No. 4,813,416, it too has certain drawbacks. The buckle is not flat because of the loop segment. However, the loop cannot be eliminated because as the band is pulled through the buckle, the buckle must be held by a clamp which engages the loop. Threading the band through the "C" flanges is sometimes difficult because of the shape of the buckle and rigidity of the flanges. Once the band is tightened, it must be trimmed. This may result in a tail with one or more sharp edges which are exposed.

The present invention is an improvement over the band of U.S. Pat. No. 4,813,416 in that the structure of the buckle has been substantially revised to make it flat by eliminating the loop segment entirely and by providing new members in the form of upstanding ears with clamp receiving openings to permit the buckle to be held firmly as the band is tightened. The ears serve a second function. They are spaced in relation to the band width such that once the band is pulled through the channel, tightened, locked and trimmed, the remaining tail can be bent back over the buckle and snap-fitted between the ears to a position proximate the buckle floor such that it is safely tucked away. Crimping the ears over the tail insures that no sharp edges are exposed, permanently locks the band and at the same time, reduces the profile of the buckle.

Threading the band into the channel in the buckle is facilitated through the use of a guide member situated on the band. More particularly, the guide member takes the form of a dome-like element situated on the surface of the band adjacent a narrowed portion. The element and the narrow band portion cooperate with the "C" shaped channel defining flanges to assist in threading the band through the channel.

It is, therefore, a prime object of the present invention to provide an improved sternum banding assembly which includes a buckle designed to be engaged by a clamp to facilitate tightening of the band but which has a low profile.

It is another object of the present invention to provide an improved sternum banding assembly which eliminates any exposed sharp edges by enclosing the trimmed tail within the buckle.

It is another object of the present invention to provide an improved sternum banding assembly wherein insertion of the band into the channel in the buckle is facilitated by a dome shaped guide element.

In accordance with one aspect of the present invention, an assembly is provided for banding the sternum. It is designed for use with a hand held clamp. The assembly includes an elongated flexible band having first and second ends. A needle extends from the first end of the band. A buckle is proximate the second end of the band. The buckle includes a surface and means cooperating with the surface defining a channel into which the band is received. Means for locking the band within the channel are provided. Means, aligned with the channel defining means and extending from the buckle surface are provided for engagement by the clamp. This permits the buckle to be retained by the clamp as the band is drawn through the channel and locked into position.

The means for engagement by the clamp includes a substantially upstanding element extending from the buckle surface. The element has an opening therein adapted to receive the clamp.

The engagement means preferably includes first and second substantially upstanding spaced elements each having an opening. The openings are adapted to receive the arms of the clamp.

The assembly preferably further includes means adapted to be retained at the end of the band, after the band is locked into position in the channel. The retaining means comprises the upstanding elements.

The end section of the band, after the band is drawn into the channel and locked into position by the locking means, is bent back over the channel defining means. The engagement means comprises means for retaining the bent end section.

The band has a given width. The upstanding elements are normally spaced apart, at their closest point, a distance which is slightly less than the band width.

The band has first and second openings. Means are provided for attaching the buckle to the band. The attaching means comprises first and second elements extending from the buckle and adapted to be received in the first and second band openings, respectively.

The band includes a portion proximate the first end. That portion includes a decreased width section and a substantially dome shaped guide element.

The channel defining means has an opening therein. The decreased width section of the band is adapted to be received within the opening.

In accordance with another aspect of the present invention, an assembly for banding the sternum is provided. The assembly is designed for use with a hand held clamp having a pair of clamp arms moveable between proximate and remote positions. The assembly includes a flexible band having first and second ends. A needle is attached to one of the ends of the band. A buckle is provided along with means for attaching the buckle proximate the other end of the band. The buckle includes a band receiving channel. Means are provided for locking the band in position within the channel. Normally spaced, substantially parallel extending elements are provided. Each element has an opening adapted to receive a different one of the clamp arms. When the clamp arms are moved from the remote position to the proximate position, the buckle is engaged and retained by the clamp as the band is drawn through the channel to the locking position.

Means are provided for retaining a portion of the band adjacent the buckle. The retaining means preferably comprises the elements.

The band has two spaced openings. The attaching means comprises spaced tab elements extending from the buckle and engaging the openings.

The band has a given width. The elements are normally spaced apart a distance slightly less than the width of the band.

The channel is defined in part by inwardly extending members spaced apart by a given distance. The band comprises a relatively narrow section and a guide member. The relatively narrow section is slightly narrower than the space between the channel defining members. The guide member is preferably substantially dome-like in configuration.

In accordance with another aspect of the present invention, a method for banding a sternum is provided. The method employs banding assembly including an elongated flexible metal band with a surgical needle fixed to one end. A buckle is mounted proximate the other end. The buckle comprises channel defining elements, a locking member and spaced upstanding ears. The ears have openings. The banding assembly is adapted for use with a clamp having arms moveable between remote and proximate positions. The method includes the steps of threading the needle and band around or through the sternum parts. The needle is then removed from the band end. The band end is guided through the channel defining elements in the buckle. The buckle is retained with a clamp by moving the arms of the clamp from the remote position to the proximate position and engaging the openings in the upstanding ears. The band is tightened by pulling it through the channel as the buckle is retained by the clamp, until the band is locked by the locking member. The excess band is cut off, leaving a tail. The band tail is bent over the channel defining elements and placed between the upstanding ears. The ears are crimped over the band.

The upstanding ears are spaced apart a distance slightly less than the width of the band. The step of placing the band tail between the upstanding ears comprises the step of snap-fitting the band tail between the ears.

To these and to such other objects are may hereinafter appear, the present invention relates to an improved sternum banding assembly, as described in detail in the following specification and recited in the annexed claims, taken together with the attached drawings, wherein like numerals refer to like parts and in which:

FIG. 7 is a perspective view of the banding assembly showing the buckle retained by a towel clamp;

FIG. 8 is a perspective view of the buckle showing the band tail being placed and the ears being crimped;

FIGS. 9(a)-9(g) collectively illustrate the steps employed to band a split sternum with the banding assembly of the present invention.

Figure 1:
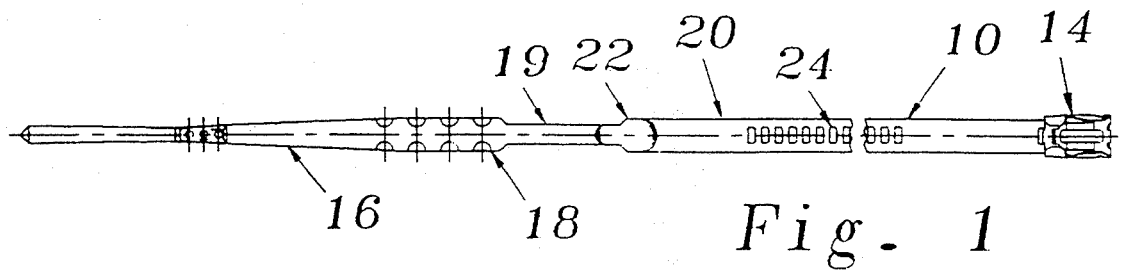
FIG. 1 is a top plan view of the banding assembly of the present invention.
Figure 2:
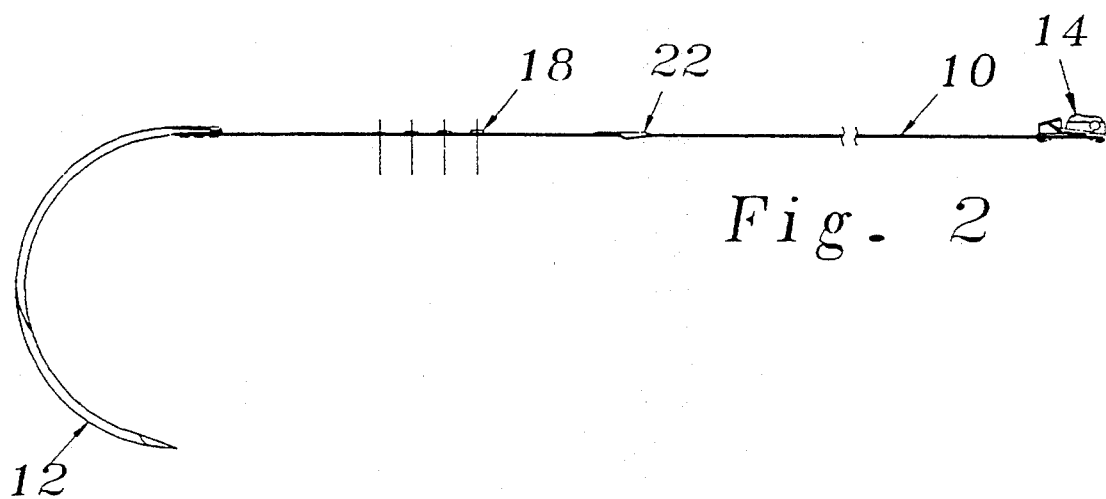
FIG. 2 is a side view of the banding assembly of FIG. 1.
Figure 3:
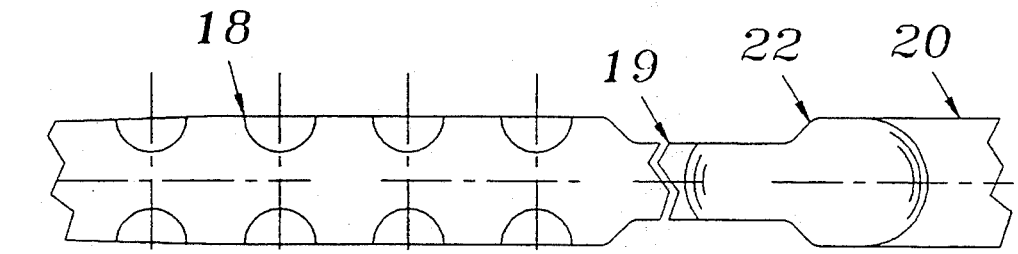
FIG. 3 is an enlarged top plan view of the band guide member.
Figure 4:
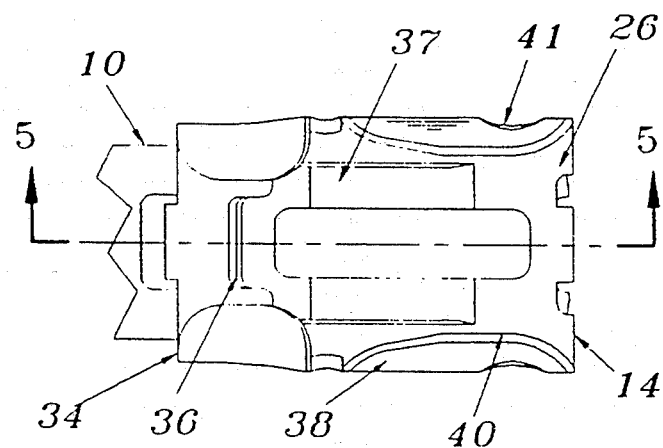
FIG. 4 is an enlarged top plan view of the buckle.
Figure 6:
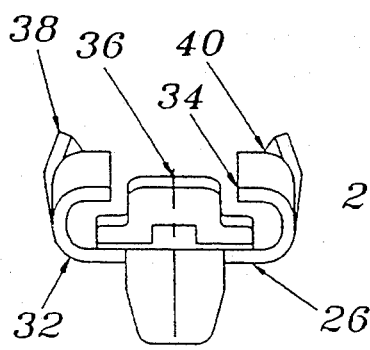
FIG. 6 is a front view of the buckle of FIG. 4, taken along line 6—6 thereof.
Figure 5:
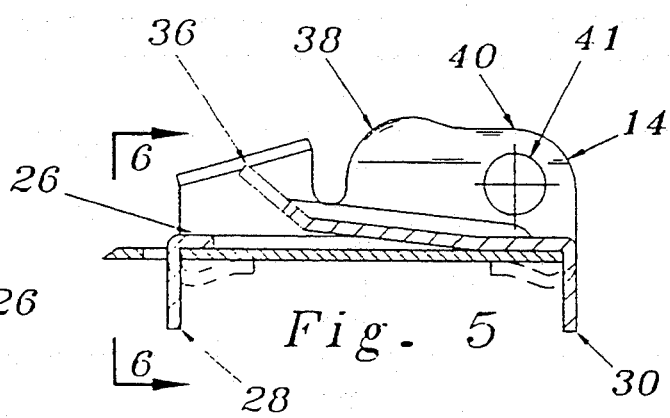
FIG. 5 is a side cutaway view of the buckle of FIG. 4, taken along line 5—5.
Figure 5A:
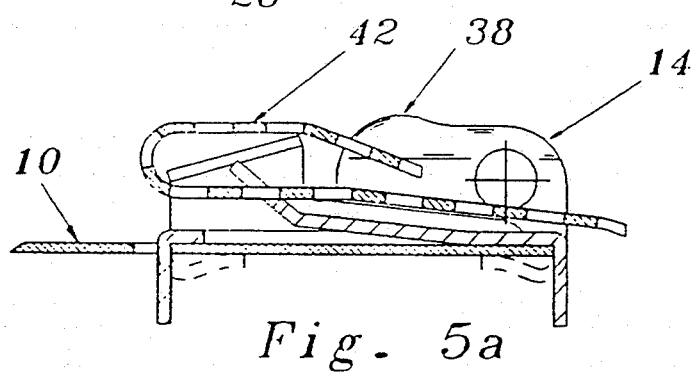
FIG. 5(a) is a side cutaway view of the buckle of FIG. 4, showing the band tail after crimping.

As seen in FIGS. 1 and 2, the banding assembly includes an elongated, thin and relatively wide flat band 10, preferably made of stainless steel. A surgical needle 12 extends from one end of band 10. Needle 12 is preferably integral with the band but may be a separate part riveted or otherwise affixed to the band. Mounted proximate the other end of band 10 is a buckle 14.

Needle 12 is curved to facilitate insertion from one parasternal location, under the sternum halves and then outwardly at an opposite parasternal location. Adjacent needle 12 is a band section 16 of gradually increasing width. Section 16 has protrusions or ripples 18 on the top surface. Ripples 18 serve to gently expand the opening in the bone to permit the band to pass through, even when kinked or distorted.

Next to ripple section 18 is a relatively narrow section 19 which widens to the main band section 20. Situated proximate the connection between sections 18 and 20 is a dome-shaped guide member 22 which extends above the band surface, preferably to the plane of the top surface of ripples 18. Member 22 facilitates entry of the main section 20 of the band into the channel in buckle 14. Main section 20 has a plurality of spaced slots 24. Slots 24 are adapted to be engaged by the locking tooth 36 in the buckle.

The buckle 14 comprises a substantially planar floor 26 having downwardly extending tabs 28, 30 at the forward and rear edge, respectively. Tabs 28, 30 are adapted to extend through spaced openings near the end of band section 20. Tabs 28, 30 are bent inwardly to secure buckle 14 to band 10.

A pair of oppositely oriented spaced "C" shaped flanges 32 extend upwardly from opposite sides of floor 26, beginning at the forward end of the buckle and extending toward the rear for approximately one third of the length of the buckle. Flanges 32 are relatively thick and rigid and define the channel into which band 10 will be received. The inwardly extending top portions 34 of the flanges are inclined upwardly, away from floor 26. Thus, the channel is wedge shaped, being smallest at its mouth and gradually becoming larger toward the rear of the buckle.

Extending upwardly from floor 26, toward the plane of top portions 34, is a locking tooth 36. Tooth 36 is adapted to be received within one of the slots 24 in band 10 to lock the band in position within the channel defined by flanges 32.

Also extending from floor 26, at either side thereof, and substantially aligned with flanges 32 are a pair of upstanding ears 38. Ears 38 are slightly curved toward each other such that the top edges 40 of the ears are the points which are closest together. Edges 40 are spaced apart by a dimension which is slightly less than the width of band section 20. The flexibility of the stainless steel material of which ears 38 are made permits a section of the band to "snap-fit" between the ears as explained below.

Ears 38 are each provided with openings 41, shaped and sized to accept the moveable arms of a conventional towel clamp. Thus, the buckle can be engaged and retained by the arms of a towel clamp as the band is pulled through the channel and tightened into the locking position such that tooth 36 protrudes into one of the slots 24 in the band.

Ears 38 serve the additional purpose of permanently retaining the tail 42 of the band, after it has been trimmed, in close face to face relation with spring element 37, in a way which covers any sharp edges of the band which may result from trimming the tail. As is explained below, once the band is locked in position in the channel, it is trimmed to have a tail with a length about as long as the buckle. The tail is bent back over flanges 32, toward the rear of the buckle, and snap fits between ears 38. Ears 38 are then crimped inwardly, covering the edges of the tail band. In this way, sharp or jagged edges are protected and a low profile is achieved.

The method of using the banding assembly of the present invention is illustrated in FIGS. 9(a)–9(g) which show the various operations involved. When the sternum is ready to be closed, needle 12 is threaded through or around the sternum sections, as shown in FIG. 9 (a). Hemostats or needle holders are used to manipulate the band and needle. Once the band is in place (FIG. 9(b)), the needle 12 is cut off, about an inch from narrow section 18. The narrow section 18 is then inserted between flanges 32 and dome-shaped member 22 guides the main section 20 of the band into the channel (FIG. 9(c)). A clamp is used to pull the band tight while the buckle is retained by a towel clamp whose arms are received in openings 41 (FIG. 9(d)). Once the band is in position, tooth 36 lodges in one of the slots 24 urged upwardly by spring element 37, to lock the band within the channel. The band is bent upwardly, 90° from floor 26 of the buckle and trimmed to form a tail 42, approximately 4 slots long (FIG. 9(e)).

Tail 42 is bent back over the buckle and particularly over flanges 32 and "snap fit" between ears 38 as illustrated in FIG. 9(f). Ears 38 are crimped to overlap the edges of the tail. (FIG. 9(g). In this way, the tail is permanently retained within the buckle and no sharp edges are exposed.

The entire procedure can be performed quickly and efficiently, using only conventional operating room instruments. The resulting structure has a low profile, with no protruding parts or sharp edges. However, the band is reliably locked by the tooth and held securely by the folded tail 42.

It should now be appreciated that the present invention relates to an improved sternum banding assembly in which spaced upstanding ears, aligned with the channel defining flanges serve as a means for engagement with a towel clamp to retain the buckle as the band is tightened and to capture the tail in a manner which covers any sharp edges which would otherwise be exposed. In addition, a dome-like guide member is employed to facilitate entrance of the main section of the band into the channel in the buckle.

While only a single preferred embodiment of the present invention has been disclosed for purpose of illustration, it is obvious that many variations and modifications could be made thereto. It is intended to cover all of these modifications and variations which fall within the scope of the invention as defined by the following claims.

I claim:

1. An assembly for banding the sternum for use with a hand held clamp, said assembly comprising an elongated flexible band having first and second ends, a needle at said first end of said band, a buckle proximate said second end of said band, said buckle comprising a surface having first and second sides, means cooperating with said surface for defining a channel into which the band is received, means for locking said band within said channel and means aligned with said channel defining means for engagement by the clamp, permitting said buckle to be retained by the clamp as said band is locked into position by said locking means, said channel defining means comprising first and second substantially upstanding elements extending respectively from said first and said second sides of said surface and said means for engagement by said clamp comprising third and fourth substantially upstanding elements aligned with said first and second upstanding elements, respectively.

2. The assembly of claim 1, wherein said band has an end section and further comprising means adapted to secure said band end section after said band is locked into position in said channel, said securing means comprising said upstanding third and fourth elements.

3. The assembly of claim 1 wherein said band has an end section and wherein said band end section, after said band is drawn into said channel and locked into position by said locking means, is bent back over said channel defining means and wherein said engaging means comprises means for securing said bent end section.

4. The assembly of claim 3 wherein said band has a given width and wherein said third and fourth elements are normally spaced apart, at their closest point, a distance which is slightly less than said given width.

5. The assembly of claim 1 wherein said band has first and second openings and further comprising means for attaching said buckle to said band, said attaching means comprising first and second elements extending from said buckle and adapted to be received in said first and second band openings, respectively.

6. The assembly of claim 1 wherein said band comprises a portion proximate said first end and wherein said portion comprises a decreased width section and a substantially dome shaped guide member.

7. The assembly of claim 6 wherein said channel defining means has an opening and wherein said decreased width section is adapted to be received within said opening.

8. The assembly of claim 1 wherein said third and fourth elements comprise clamp receiving openings.

9. The assembly of claim 1 wherein said first end of said band has an end section and wherein said third and fourth elements are adapted to receive said end section therebetween.

10. The assembly of claim 9 wherein said third and fourth elements are adapted to be bent over said band end section to cover said band end section.

* * * * *